United States Patent [19]

Kastendieck

[11] Patent Number: 4,942,177

[45] Date of Patent: Jul. 17, 1990

[54] COMPOSITION AND METHOD FOR CLEANING AND SANITIZING THE TEATS OF MILK PRODUCING ANIMALS

[76] Inventor: Keith G. Kastendieck, Rte. 1 Box 410, Washington, Mo. 63090

[21] Appl. No.: 269,198

[22] Filed: Nov. 9, 1988

[51] Int. Cl.$^5$ .............................................. A01N 37/00
[52] U.S. Cl. .................... 514/560; 252/106; 514/873
[58] Field of Search ............... 514/558, 578, 873, 560; 252/106; 424/78

[56] References Cited

U.S. PATENT DOCUMENTS

| | | | |
|---|---|---|---|
| Re. 29,814 | 10/1978 | Snyder | 424/81 |
| 2,396,012 | 3/1946 | Jones | 424/78 |
| 2,576,987 | 12/1951 | Wyman | 424/88 |
| 2,841,526 | 7/1958 | Gustus | 167/55 |
| 3,445,565 | 5/1969 | Locker | 424/46 |
| 3,867,533 | 2/1975 | Schmolka | 424/78 |
| 3,932,602 | 1/1976 | Sweger | 424/45 |
| 3,950,554 | 4/1976 | Prince | 514/873 |
| 4,199,564 | 4/1980 | Silver | 424/78 |
| 4,406,884 | 9/1983 | Fawzi et al. | 514/558 |
| 4,520,132 | 5/1985 | Kinsolving | 514/560 |
| 4,548,807 | 10/1985 | Westfall et al. | 424/45 |

FOREIGN PATENT DOCUMENTS 83-00163  1/1983  World Int. Prop. O. .......... 252/106

OTHER PUBLICATIONS

Antimicrobial in Foods–1983–Ed. Branen and Davidson–p. 119.

*Primary Examiner*—Douglas W. Robinson
*Attorney, Agent, or Firm*—Robbins & Robbins

[57] ABSTRACT

A composition and method for preparation of a cleaner and sanitizer for teats of dairy animals. Water insoluble sodium undecylenate is formed in situ in an aqueous blend of food additive, germicidal, cosmetic, and detergent components, resulting in a cleaner and sanitizer for dipping the teats of milk producing animals prior to and subsequent to milking. The composition may also include emollients for skin conditioning.

11 Claims, No Drawings

COMPOSITION AND METHOD FOR CLEANING AND SANITIZING THE TEATS OF MILK PRODUCING ANIMALS

BACKGROUND OF THE INVENTION

In the dairy industry, it is important to maintain a clean, sanitized environment to prevent contamination and spoilage of the dairy products. Because the milk is drawn from a living animal, the potential exists for contamination of the milk via the donor animal itself. The tests of milk producing animals are quite susceptible to various pathogenic bacterial organisms which may thrive on the teat exterior or may gain entrance into the teat canal.

Great capital expenditures are made to ensure that the processing, packaging and distribution of dairy products is done in a clean and sanitary manner. It is prudent, therefore, to ensure that the first step of drawing the milk from the animal is also done under clean and sanitary conditions. Unless this is done, great losses could be sustained by the migration of infectious organisms from the external surface of the cows teat into the milk.

A variety of cleaning products are currently available using active germicides such as iodine, sodium hypochlorite, chlorhexidine, quarternary ammonium compounds and DDBSA. These products, however, are limited in their effectiveness and have a narrow range of the type of infectious organisms killed.

While the employment of undecylenic acid and other unsaturated acids and their salts for combatting bacteria are shown in the prior art, there is not shown any topical application with non-irritating, skin conditioning emollients to the teats of milk producing animals for cleaning and sanitizing prior to and subsequent to milking to minimize bacterial entrance into the teat canal or the recovered milk. Nor is there shown any feature whereby there is safe use in the event of any introduction of the undecylenic acid composition into the milk.

SUMMARY OF THE INVENTION

By means of this invention there has been provided a composition, and its method for production, for cleaning and sanitizing the surface of the teats of milk producing animals prior to and after milking and to minimize bacterial entrance into the teat canal.

The composition consists of an aqueous solution of the germicide sodium undecylenate which has broad spectrum kill against gram positive pathogenic organisms such as *staph aureus* and gram negative environmental organisms such as pseudomonas and *E. coli*, which are more frequently the cause of infectious mastitis.

The cleaning and sanitizing composition of this invention may also include emollients for skin conditioning. Appropriate organic solvents which are non-irritating to the skin and can function as both solvents and skin-conditioning emollients include, but are not limited to, fatty acid esters and their derivatives, lanolin and its derivatives, glycerin, glycerol esters and their derivatives, sorbitol, sorbitol esters and their derivatives, and polyethylene glycol and its derivatives.

The cleaning and sanitizing composition of this invention incorporates approved food additive materials in both the active and inactive ingredients thus making its use as a germicide safe in the event that residues of the composition migrate from the external surface of the animals teat into the milk during production.

By means of this invention there has also been provided a method for production of the composition by blending a water insoluble sodium undecylenate into an aqueous blend of food additive, germicidal, cosmetic, and detergent components. The composition of this invention cannot be practically made using the commercially available aqueous salts of undecylenic acid, or by changing the sequence of addition of the components. The composition is made by first dissolving a water soluble organic solvent, which may be an emollient, in water and then slowly adding the water insoluble, or difficulty soluble, undecylenic acid to this mixture. After the acid is completely dissolved, a neutralization base is slowly added until a neutral pH is achieved to form dissolved sodium undecylenate in situ in the solution.

The above features are objects of this invention. Further objects will appear in the detailed description which follows and will be otherwise apparent to those skilled in the art.

DESCRIPTION OF THE INVENTION

The composition of this invention incorporates a blend of water insoluble sodium undecylenate in an aqueous blend of approved food additive active and inactive ingredients to provide an efficacious cleaner for dipping the teats of milk producing animals and especially dairy cattle prior to milking and after milking. The food additive components in addition to the sodium undecylenate may comprise germicidal, cosmetic and detergent components.

The composition is made by forming the sodium undecylenate in situ in solution in the aqueous composition. This is effected by first dissolving a water soluble organic solvent in water and then slowly adding undecylenic acid, which is water insoluble, to the aforesaid solution. After the acid is completely dissolved the neutralization base, which in the preferred form is sodium hydroxide, is slowly added with good agitation until a neutral pH of about 7 is obtained. The organic solvent, which in the preferred form is propylene glycol, not only provides a solution for the undecylenic acid but also provides desirable emollient characteristics to the composition for application to the teats of the dairy animal besides being a safe food additive.

The sequence of addition of the components has been found to be necessary to form the sodium undecylenate since the cleaning and sanitizing composition can not be made using commercially available aqueous salts of undecylenic acid or by changing the sequence of addition of the components. Further, it has been found that metallic cations, commonly found in water, such as calcium, magnesium and iron will react with the anionic part of some neutralization bases resulting in an undesirable cloudy solution and incomplete solubilization of the undecylenic acid. This problem can be alleviated by using softer water or by the addition of small amounts of chelating agents such as ethylene diamine tetra acetic acid, commonly referred to as EDTA.

The neutralization bases to provide the salts of undecylenic acid may be the hydroxides or carbonates of sodium, potassium or lithium or ammonium hydroxide.

The organic solvents employed are those which function as solvents for undecylenic acid, skin conditioners that are non-irritating to the skin and are approved food additives. Such solvents comprise propylene glycol, glycerin, sorbitol, polyethylene glycol, glycol, polyethylene glycol fatty acid estors, ethoxylated glycerin and sorbitol esters.

There is set forth below a typical example in which the components are added in order of addition starting with water.

| water | 87.15% |
|---|---|
| F. D. & C. Blue #1 dye | .00065% |
| tetra sodium EDTA 50% | .25% |
| propylene glycol | 10.00% |
| undecylenic acid | 1.90% |
| sodium hydroxide 50% | .70% |

This formula provides 2.2% sodium undecylenate with a pH of 6.0 to 8.0 and specific gravity of 1.01 g/ml at 25° C.

The composition from the above example is employed at full strength upon the teats of cows or other milk producing animals such as sheep and goats as will be readily understood. The application is by standard means such as spraying, swabbing, washing, dipping or the like.

The composition has been tested against standard bacteria and has shown very good anti-microbial activity. Such a test has been carried out using a standard AOAC 14 Test for Germicidal Detergents and Sanitizers, modified. In this test 10 ml of the test product, made according to the example described above, undiluted, was placed into sterile 25×150 mm test tubes and placed in a 37° water bath for 5 minutes. Then, 1 ml of the test organism was added to the test solution and mixed by rotation. At intervals of 2, 5 and 10 minutes a 1 ml aliquot was removed from the test solution and added to 9 ml of Letheen Broth. Serial dilutions were made in additional 9 ml volumes of Letheen Broth and plated using Aerobic Plate Count procedure. Plated aliquots were poured with Letheen Agar. Test plates were incubated at 35° for 48 hours. The test organisms were *E. Coli* which is commonly found in feces, intestines and water, and *Streptococcus agalactiae* which is normally present in dairy animals.

| Percent Reduction of Test Organisms from To Counts | | | |
|---|---|---|---|
| | Time in Minutes | | |
| Test Organism | 2 | 5 | 10 |
| E. Coli (ATCC 8739) | 99.99999 | 99.99999 | 99.99999 |
| S. agalactiae (midwest) | 99.99999 | 99.99999 | 99.99999 |
| Inocula Counts (Log 10 in pH 7.2 Buffer) To | | | |
| E. Coli ATCC 8739 | | | 9.1205 |
| Streptococcus agalactiae | | | 9.1958 |

*Mean of duplicate platings.

The composition of this invention lends itself to safe and efficacious employment by the dairy industry. The application to the teats of the cows or other dairy animals is effected at full strength by standard means of application. There is no requirement of rigorous safety controls since all the components are standard and approved food additives. It will be understood that the formulation represents a preferred composition and that obvious changes and variations in proportions may be effected by those skilled in the art.

Various changes and modifications may be made within this invention as will be apparent to those skilled in the art. Such changes and modifications are within the scope and teaching of this invention as defined in the claims appended hereto.

What is claimed is:

1. A disinfectant and sanitizing composition for teats and udders of milk producing dairy animals, said composition consisting essentially of food additive materials which are harmless to milk produced subject to migration of the composition from said teats into the milk, said composition having a pH of about 7 and consisting essentially of an aqueous solution of an effective amount of sodium undecylenate as a disinfectant and sanitizing agent and a water soluble organic solvent for said sodium undecylenate, said organic solvent having an emollient characteristic and comprising at least one member of the group consisting of propylene glycol, glycerin, sorbitol, polyethylene glycol, polyethylene glycol fatty acid esters, ethoxylated glycerin, glycol and sorbitol esters.

2. The composition of claim 1 in which the sodium undecylenate is present in the amount of about 2%.

3. The composition of claim 2 in which the organic solvent is propylene glycol, said propylene glycol being present in the amount of about 10%.

4. The composition of claim 2 in which sodium ethylene diamine tetraacetic acid is present in the amount of about 0.25%.

5. The composition of claim 1 in which water is present in the amount of about 87% and the sodium undecylenate is present in the amount of about 2%.

6. The composition of claim 5 in which the organic solvent is propylene glycol, said propylene glycol being present in the amount of about 10%.

7. The composition of claim 5 in which the organic solvent is propylene glycol, said propylene glycol being present in the amount of about 10% and sodium ethylene diamine tetraacetic acid is present in the amount of about 0.25%.

8. A method for cleaning and sanitizing the surfaces of the teats and udder of milk producing animals which comprises applying a cleaning and sanitizing composition to said surfaces prior to and subsequent to milking, said composition consisting essentially of food additive materials which are harmless to milk produced subject to migration of the composition from said teats into the milk, said composition having a pH of about 7 and consisting essentially of an aqueous solution of an effective amount of sodium undecylenate as a cleaning and sanitizing agent and a water soluble organic solvent for said sodium undecylenate, said organic solvent having an emollient characteristic and comprising at least one member of the group consisting of propylene glycol, glycerin, sorbotol, polyethylene glycol, polyethylene glycol fatty acid esters, ethoxylated glycerin, glycol and sorbitol esters.

9. The method of claim 8 in which the sodium undecylenate is present in the amount of about 2% and the organic solvent is propylene glycol, said propylene glycol being present in the amount of about 10%.

10. The method of claim 8 in which the organic solvent is propylene glycol, said propylene glycol being present in the amount of about 10% and water is present in the amount of about 87% and the sodium undecylenate is present in the amount of about 2%.

11. The method of claim 10 in which sodium ethylene diamine tetraacetic acid is present in the amount of about 0.25%.

* * * * *